US011647995B2

(12) United States Patent
Peterson et al.

(10) Patent No.: US 11,647,995 B2
(45) Date of Patent: May 16, 2023

(54) SAMPLE CASSETTE FOR COLLECTING TISSUE SAMPLES FROM A FLUID STREAM, THE CASSETTE INCLUDING PLURAL CATCH TRAYS FOR RETAINING PLURAL SAMPLES

(71) Applicant: Stryker Corporation, Kalamazoo, MI (US)

(72) Inventors: Michael Peterson, Richland, MI (US); Chamara L. Gamhewage, Kalamazoo, MI (US); Andrew J. Nollar, Portage, MI (US); Stephen J. Reasoner, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 675 days.

(21) Appl. No.: 16/072,062

(22) PCT Filed: Jan. 19, 2017

(86) PCT No.: PCT/US2017/014128
§ 371 (c)(1),
(2) Date: Jul. 23, 2018

(87) PCT Pub. No.: WO2017/127541
PCT Pub. Date: Jul. 27, 2017

(65) Prior Publication Data
US 2019/0038195 A1 Feb. 7, 2019

Related U.S. Application Data

(60) Provisional application No. 62/281,250, filed on Jan. 21, 2016.

(51) Int. Cl.
*A61B 10/02* (2006.01)
*A61M 1/00* (2006.01)
*A61B 5/157* (2006.01)

(52) U.S. Cl.
CPC .............. *A61B 10/02* (2013.01); *A61B 5/157* (2013.01); *A61M 1/00* (2013.01); *A61M 1/71* (2021.05);
(Continued)

(58) Field of Classification Search
CPC ....... A61B 10/02; A61B 10/0096; B01L 3/50; B01L 3/508; B01L 2400/0633;
(Continued)

(56) References Cited

U.S. PATENT DOCUMENTS 5,170,801 A 12/1992 Casper et al.
5,256,160 A * 10/1993 Clement ............ A61B 18/1482
220/502

(Continued)

FOREIGN PATENT DOCUMENTS

CN 102500000 A 6/2012
CN 104321647 A 1/2015

(Continued)

OTHER PUBLICATIONS

International Search Report for Application No. PCT/US2017/014128 dated Jun. 13, 2017, 3 pages.

(Continued)

*Primary Examiner* — Devin B Henson
*Assistant Examiner* — H. Q. Nguyen
(74) *Attorney, Agent, or Firm* — Howard & Howard Attorneys PLLC

(57) ABSTRACT

A cassette for retrieving plural tissue samples from a fluid stream. The cassette includes a bypass conduit and plural voids. A catch tray is removably seated in each of the voids. A fitting extends from the cassette. The cassette has an outlet opening through which a suction is drawn. The cassette also has a valve. The valve directs the fluid stream from the (Continued)

fitting so the fluid stream flows through the bypass conduit or through one of the voids in which a catch tray is seated.

18 Claims, 8 Drawing Sheets

(52) U.S. Cl.
CPC ................ *A61M 1/72* (2021.05); *A61M 1/79* (2021.05); *A61M 2202/09* (2013.01); *A61M 2205/75* (2013.01)

(58) Field of Classification Search
CPC ......... B01L 2300/049; A61M 2205/75; A61M 1/0023; A61M 1/0035; A61M 1/0043; A61M 1/0056; A61M 1/005; A61M 1/60; A61M 1/71; A61M 1/72; A61M 1/79
See application file for complete search history.

(56) References Cited

U.S. PATENT DOCUMENTS

| | | |
|---|---|---|
| 5,624,418 A | 4/1997 | Shepard |
| 6,375,625 B1 * | 4/2002 | French ................ A61M 1/0001 600/573 |
| 6,506,168 B1 | 1/2003 | Fathallah et al. |
| 6,571,792 B1 | 6/2003 | Hendrickson et al. |
| 6,925,317 B1 | 8/2005 | Samuels et al. |
| 8,702,623 B2 | 4/2014 | Parihar et al. |
| 9,945,821 B2 | 4/2018 | Kriel et al. |
| 10,105,470 B2 | 10/2018 | Reasoner et al. |
| 10,722,617 B2 | 7/2020 | Murray et al. |
| 2007/0135779 A1 | 6/2007 | Lalomia et al. |
| 2007/0270714 A1 * | 11/2007 | Cushner ................ A61B 10/04 600/571 |
| 2011/0106029 A1 | 5/2011 | Garren et al. |
| 2012/0053484 A1 | 3/2012 | Parks |
| 2014/0323914 A1 | 10/2014 | VanderWoude et al. |
| 2018/0344299 A1 | 12/2018 | Keller et al. |

FOREIGN PATENT DOCUMENTS

| | | |
|---|---|---|
| CN | 104936631 A | 9/2015 |
| WO | 2007070570 A2 | 6/2007 |
| WO | 2013090579 A1 | 6/2013 |

OTHER PUBLICATIONS

English language abstract for CN 104321647 extracted from espacenet.com database on Aug. 3, 2020, 2 pages.
English language abstract for CN 102500000 extracted from espacenet.com database on Aug. 3, 2020, 2 pages.
English language abstract for CN 104936631 extracted from espacenet.com database on Aug. 3, 2020, 2 pages.

* cited by examiner

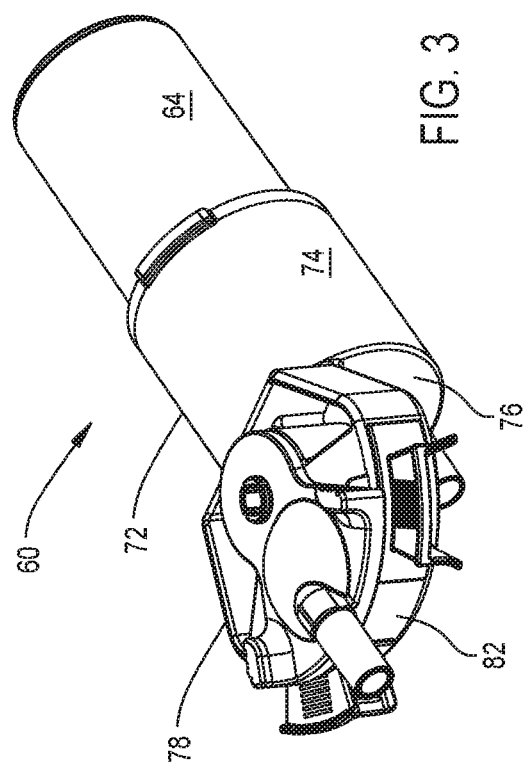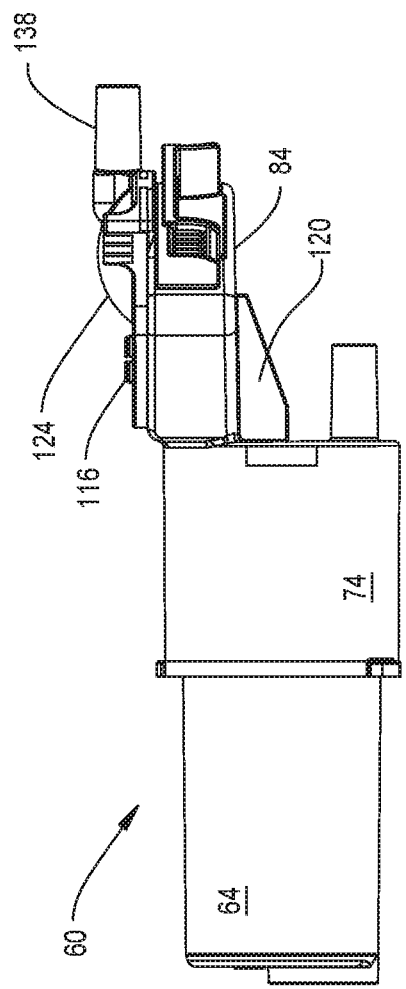

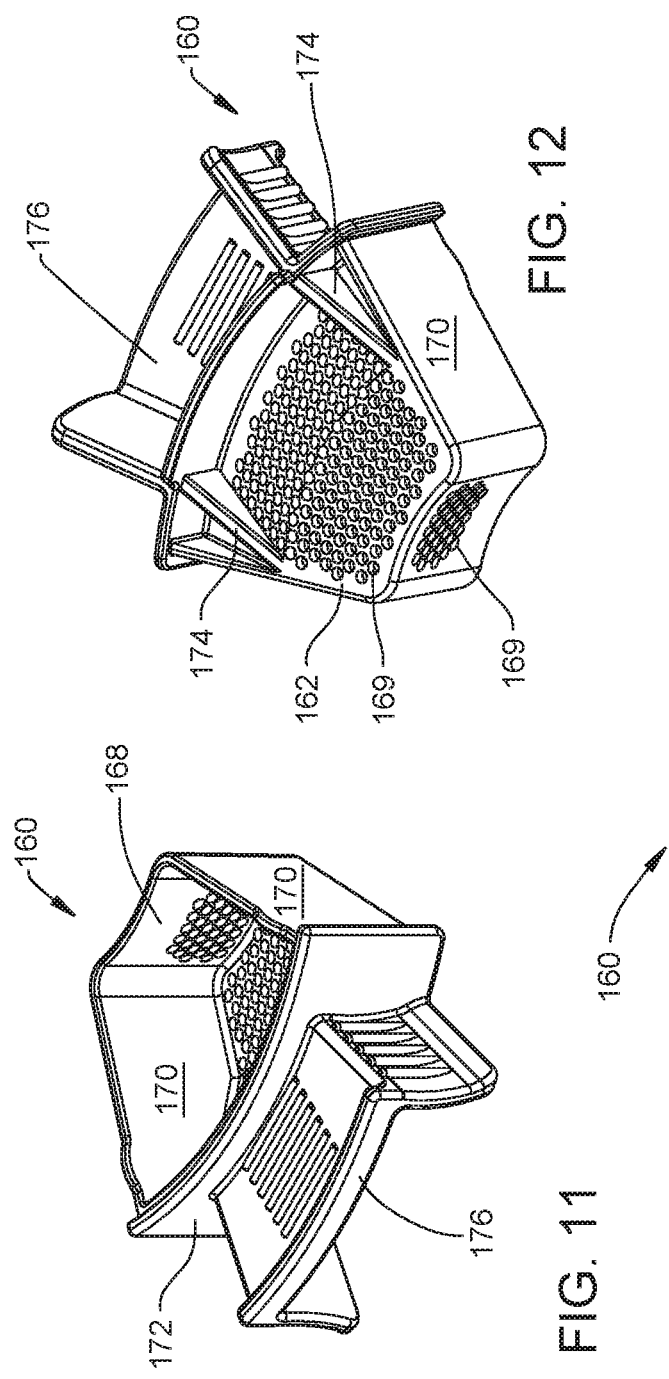
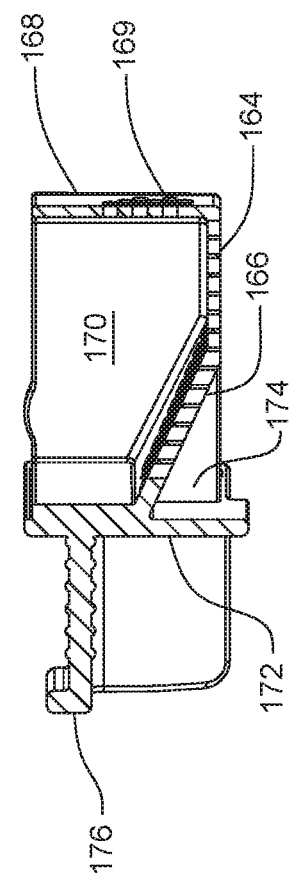

SAMPLE CASSETTE FOR COLLECTING TISSUE SAMPLES FROM A FLUID STREAM, THE CASSETTE INCLUDING PLURAL CATCH TRAYS FOR RETAINING PLURAL SAMPLES

This application is a U.S. National Stage of International Patent Application No. PCT/US2017/014128, filed on Jan. 19, 2017, which claims the benefit of and priority to U.S. Provisional Patent Application Ser. No. 62/281,250, filed on Jan. 21, 2016, the entire contents of each is hereby incorporated by reference in its entirety.

FIELD OF THE INVENTION

This invention relates generally to a system and method for collecting waste fluid and retrieving tissue samples generated during a surgical procedure. More particularly, this invention relates to a system and method for retrieving plural samples without having to appreciably interrupt the flow of waste fluid from the site at which the procedure is performed.

BACKGROUND OF THE INVENTION

A byproduct of the performance of some medical and surgical procedures is the generation of liquid, semi-solid and solid waste. This waste includes body fluids, such as blood, and irrigating solution that are introduced to the body site at which the procedure is performed. Solid and semi-solid waste generated during a procedure includes bits of tissue and small pieces of the surgical material that may be left at the site. Ideally, the waste is collected upon generation so the waste neither visually obstructs nor fouls the surgical site nor becomes a biohazard in the operating room or other location at which the procedure is being performed.

A number of systems are available for use by surgical personnel for collecting this waste as it is generated. Generally, this type of system includes a suction source, tubing that extends from the suction source and a storage container between the tubing and the suction source. When the system is actuated, waste is drawn through the distal end of the tubing. The suction draws the waste through the tubing so that it flows into and is at least temporarily held in the storage container. One such system is Applicant's US Pat. Pub. No. US 2007/0135779 A1/PCT Pub. No. WO 2007/070570 A2, the contents of which is incorporated herein by reference.

In some surgical procedures, such as a colonoscopy, it is desirable to collect one or more tissue samples from the patient during the surgical procedure. The tissue sample typically is sent to a pathology lab for analysis. The analysis of the sample aids in the evaluation of the medical state of the patient from which the sample was collected. To collect a tissue sample, the tubing connecting the medical instrument used to apply suction to the patient to a waste container may be temporarily disconnected. A separate device is placed in series with the tubing so as to be located upstream from the container. The tissue sample is captured in the device. The device is then removed and the tubing from the suction applicator is reconnected directly to the waste container. Repetitive connecting and disconnecting of the tubing during the collection of multiple samples adds additional time to the completion of the surgical procedure. Upon disconnection of the tubing, small amounts of adhered uncontained liquid and semisolid waste in the tubing can be released into the surrounding environment potentially contaminating the floors and other surfaces in the surgical facility.

A solution to this problem is offered in the Applicant's US Pat. Pub. No. US 2014/0323914 A1/PCT Pub No. WO 2013/090579 A1, the contents of which is incorporated herein by reference, discloses a number of different cassettes designed for removable attachment to a suction system. These cassettes include each include a removable tissue trap. The tissue trap is formed with a screen that allows fluid to flow through while retaining bits of matter, typically matter at least 1 mm in size. A number of these cassettes each include a set of conduits and valve. The conduits and valve are designed to flow the fluid stream drawn into the system along one of two paths. When the fluid stream does not include tissue in need of collection, the valve is set so the withdrawn fluid bypasses the tissue trap as the fluid flows into the storage container. During the procedure, tissue that worthy of study may become entrained in the suction flow. When the practitioner becomes aware that this event is about to occur, the cassette valve is set from the bypass position to the collection position. When the valve is so set the fluid flows along a path that extends across the tissue trap. The tissue to be collected is trapped by the screen integral with the tissue trap. Once the sample is trapped, the valve is returned to the bypass position.

The trap of the above described cassette can be used to capture plural samples. A disadvantage of this practice is that is that when plural samples are trapped, it is not possible to determine, for each sample, the location internal to the patient from which the samples was extracted. The inability to so differentiate between the individual samples reduces the utility of this type of cassette in a procedure in which there is a likelihood that there is a need to capture plural samples. This is because in order to evaluate the condition of the patient it is important to know not just the pathology of the sample, but the precise location on or in the patient's body from which the sample was extracted.

Accordingly, to use this type of cassette to collect plural samples it is necessary to, after a sample is collected, stop the withdrawal of material from the patient. During this suspension period, at a minimum, a new trap needs to be fitted to the cassette. Alternatively, a new cassette must be substituted for the used cassette. In either situation, this suspension of the procedure increases the overall time it takes to perform the procedure. Having to so extend the time it takes to perform the procedure is contrary to one of the generally objectives associated with perform a medical or surgical procedure. This is the objective that the procedure should be performed as quickly as possible. This efficiency desirable to both minimize the amount of time the patient is held under anesthesia and that patient's normally covered internal tissue is exposed to the ambient environment and infecting-inducing agents that are essentially inevitably present in this environment.

Still another disadvantage of some cassettes is that it is possible to withdraw the trap while the valve is set to allow a suction to be drawn on the cassette. These specimens can be relatively light in weight. When the cassette is withdrawn while the valve is in this state a light weight specimen can inadvertently be drawn into the container. For most intents and purposes, this results in the loss of the specimen for analysis.

SUMMARY OF THE INVENTION

This invention is related to a new and useful trap for collecting tissue that is withdrawn from a patient during a medical or surgical procedure. The assembly of this invention is constructed to allow the rapid capture of plural samples, each in its own trap, without requiring an appreciable interruption of the suction draw from the site at which the samples are withdrawn.

This invention is in the form of a cassette that is placed between the suction line through which the sample containing fluid stream is withdrawn and the suction pump that draws the fluid stream from the patient. Typically, the cassette is placed between suction line and the container used to hold the fluid drawn away from the patient.

The cassette has, at the distal end, a fitting to which the suction line is attached. The cassette has, at a proximal end, an opening through which the suction is drawn by the pump. Internal to the cassette are plural voids. These voids are open to the outside. The cassette is formed to define plural flow paths. One flow path extends from each void to the opening in the proximal end of the cassette. There is also an additional flow path, a bypass flow path. This additional flow path does not extend from the voids. Instead, this flow path leads directly to the proximal end opening in the cassette.

The cassette of this invention includes a valve. The valve directs the fluid flow from the fitting so the fluid flows into either a select one of the plurality of the voids or the flow path that bypasses the voids.

Also part of this invention are plural catch trays. The catch trays are shaped to removably be received in the voids internal to the cassette. A catch tray is designed to allow fluid flow through the tray while retaining an object beyond a certain size, the size of a sample, in the tray. Each catch tray can be independently inserted into and removed from the associated void without requiring the insertion or removal of another one of the catch trays.

In some versions of the invention, the fitting is part of the valve. In some versions of the invention, the valve is rotatably attached to the rest of the cassette. The rotational orientation of the valve relative to the rest of the cassette shifts relative to the setting of the valve.

In some versions of the invention the cassette and attached components are part of an assembly known as a manifold. This manifold serves as the removable interface that connects a suction line to a waste collection unit. In these versions of the invention, the manifold may also include a filter. This filter is located between the catch trays and the proximal end opening of the cassette. This filter prevents material not captured in one of the sample trays from flowing into the container used to hold the withdrawn fluid.

This invention is also related to a new and useful cassette that prevents the withdrawal of the trap when the valve is in the collection position, the position in which the valve directs fluid flow through the tray. In these versions of the invention a lock out is connected to the valve. When the valve is in the trap position the lock out abuts the tray so as to prevent removal of the tray. When the valve is set to direct the fluid stream away from a particular catch tray, the movement of the valve results in a like movement of the lock out. In some versions of the invention the lock out is integrally formed with the valve. Alternatively, valve and lock out are separate components. A linkage connects the lock out to the valve so that when the valve moves away from a specimen collection position, the lock out moves away from the associated catch tray.

BRIEF DESCRIPTION OF THE DRAWINGS

The invention is pointed out with particularity in the claims. The above and further features and benefits of this invention are understood by reference to the following Detailed Description taken in conjunction with the accompanying drawings in which:

FIG. 3 is a perspective view of the manifold;

FIG. 4 is a side plan view of the manifold;

FIG. 11 is a perspective view of the top of the catch tray;

FIG. 12 is a perspective view of the bottom of the catch tray;

FIG. 13 is a cross sectional view of the catch tray;

DETAILED DESCRIPTION

Figure 1:
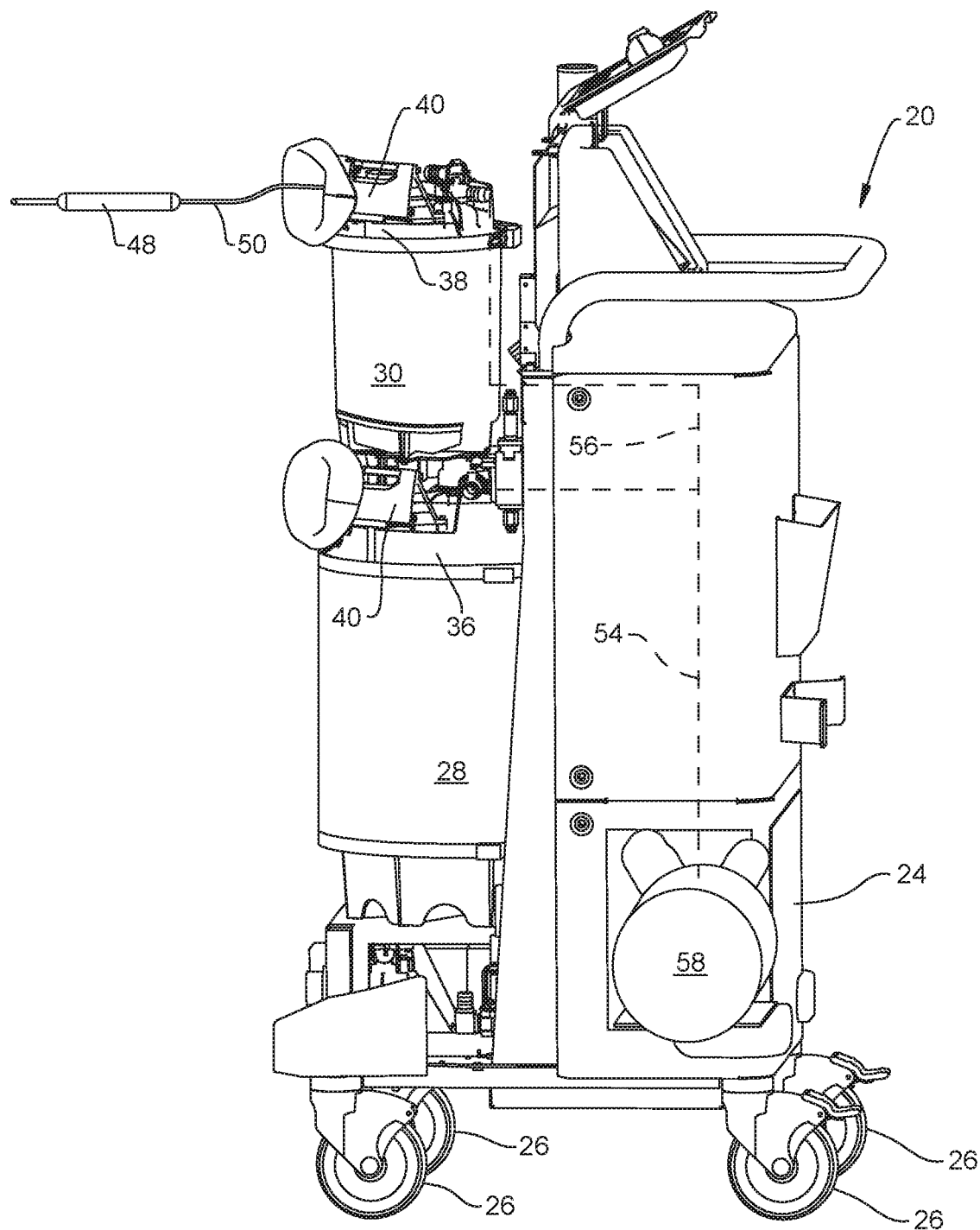
FIG. 1 depicts a surgical waste collection unit to which a form of a cassette of this invention, a manifold, is mounted.

FIG. 1 illustrates a waste collection unit 20 to which a sample cassette 60 of this invention is coupled. In some versions of the invention, cassette 60 is referred to as a manifold. Accordingly, in this document manifold 60 is understood to be the cassette 60. In the illustrated version of the invention, waste collection unit 20 is mobile. The waste collection unit 20 includes a base 24. The cover and door assemblies that normally conceal the components are mobile unit 20 are not present in FIG. 1 so that the normally concealed components can be seen. Wheels 26 attached to the bottom of the base 24 provide waste collection unit 20 with mobility. Two canisters 28 and 30 are mounted to the base 24. A first one of the canisters, canister 28, has a relatively large interior volume, between approximately 10 and 40 liters. The second canister, canister 30, has a smaller volume, between approximately 1 and 10 liters. Each canister 28 and 30 has a cap 36 and 38, respectively.

Figure 2:
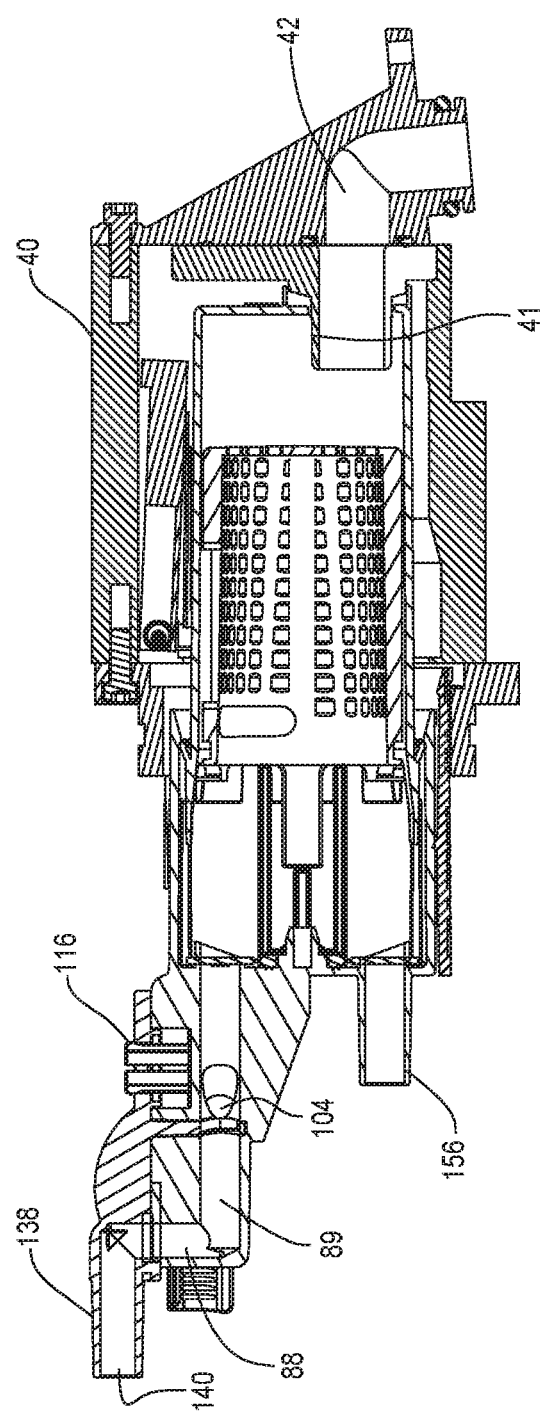
FIG. 2 illustrates in cross section the manifold of this invention seated in the receiver of the waste collection unit.

Attached to each canister cap 36 and 38 is a manifold receiver 40. A manifold 60 of this invention, seen in FIGS. 2 and 3, is removably seated in each manifold receiver 40. Each manifold 60 includes a fitting 138. Fitting 138 receives a separate suction line 50, (one shown in FIG. 1). The distal end of each suction line 50 is attached to a suction applicator 48. ("Distal," it is understood means towards the surgical site at which the suction is applied. "Proximal" means away from the surgical site.) While in FIG. 1, suction applicator 48 is shown as handpiece specifically and solely designed to apply suction, it should be understood that this is exemplary, not limiting. Sometimes the suction applicator 48 is built into another surgical tool, such as an endoscope or ablation tool, applied to surgical site to accomplish a task other than applying suction. Sometimes the suction applicator 48 is the open distal end of the suction line 50.

Internal to each manifold receiver 40 is a fitting 41. A conduit 42 extends from the fitting 41. Conduit 42 functions as a fluid communications path from the manifold 60 into the canister 36 or 38 with which the receiver 40 is associated.

Also part of mobile unit 20 is a suction pump 58. Conduits 54 and 56, (shown as dashed lines in FIG. 1) connect each canister 36 and 38 to the inlet port of the suction pump 58. When suction pump 58 is actuated, the resultant suction draws matter into the suction applicator 48 and through the associated suction line 50, manifold 60 and manifold receiver 40. The waste stream flows from the manifold receiver 40, through conduit 42 into the associated canister 36 or 38. Liquid and small solid bits of matter entrained in this flow stream precipitate out of the stream into the canister 36 or 38. This waste is stored in the canister 36 or 38 until the canister is emptied. Gas and small bits of matter entrained in this flow stream flow from the canister towards the suction pump 58. Filters, not illustrated and not part of this invention, trap the viral and bacterial-sized matter and some of the components of the gas in this fluid stream prior to the stream being drawing into and exhausted out of the suction pump 58.

Figure 5:
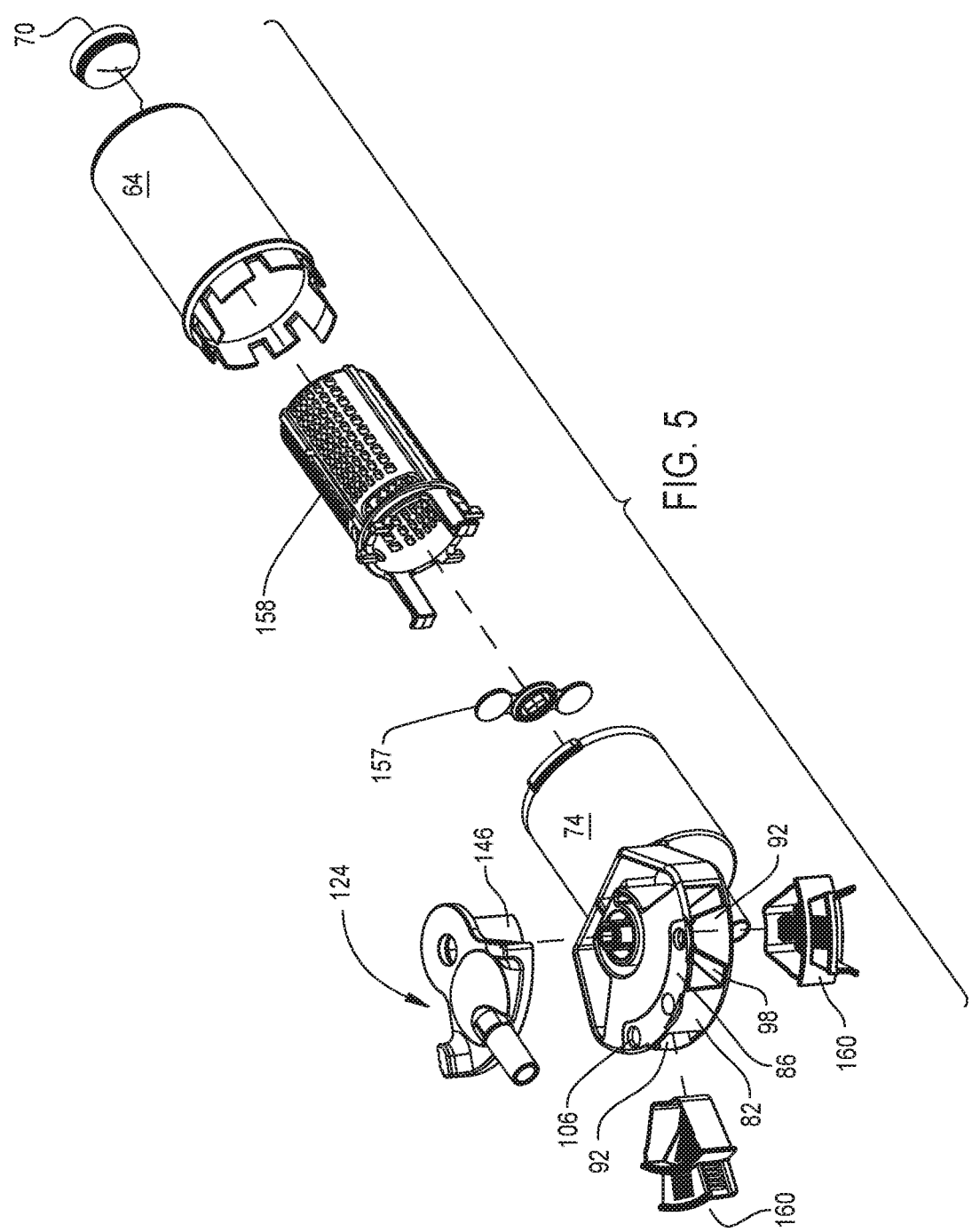
FIG. 5 is an exploded view of the manifold.

As seen best in FIGS. 3-5, the proximal portion of manifold 60 is an open ended shell 64. A cap 72 covers the open distal end of the shell 64. Collectively, the shell 64 and cap 72 forming the body or housing of the manifold 60. Shell 64 and cap 72 are further collectively dimensioned to define a void space internal to the manifold body, (void space not identified).

Figure 6:
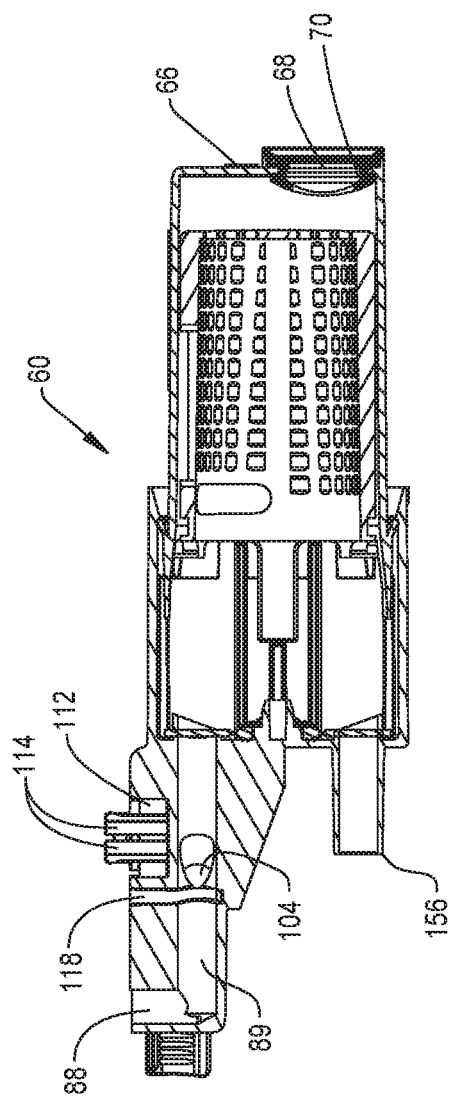
FIG. 6 is a cross section view of the manifold.

The shell 64 is generally tube like in shape. The shell 64 is the portion of the manifold dimensioned to seat in an open ended bore in the manifold receiver 40. Shell 64 is further formed to have, at the proximal end, a circularly shaped base plate 66. Base plate 66 is formed to have an opening 68. Opening 68 provides a fluid communications path from the void space internal to the manifold. The opening 68 is dimensioned to receive the fitting 41 internal to the manifold receiver 40. A drip stop 70, seen only in FIGS. 5 and 6, is disposed over opening 68. When the manifold 60 is disconnected from the receiver 40, the drip stop 70 prevents fluid flow out of the opening 68.

Figure 7B:
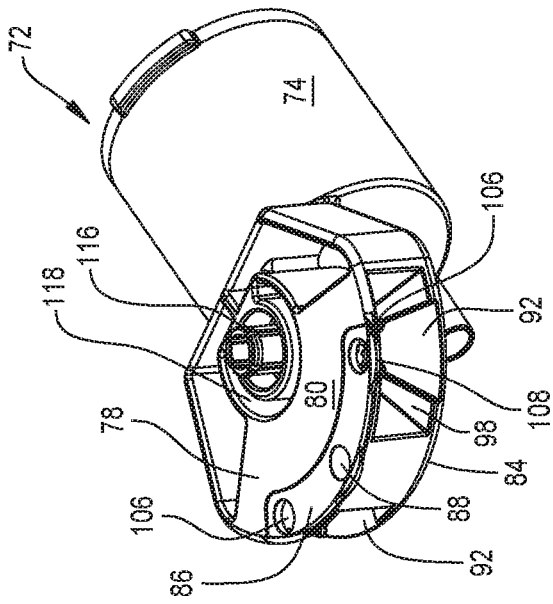
FIGS. 7A and 7B are perspective views of the head of the manifold, in FIG. 7A the valve is attached to the manifold, in FIG. 7b, the valve is removed.
Figure 7A:
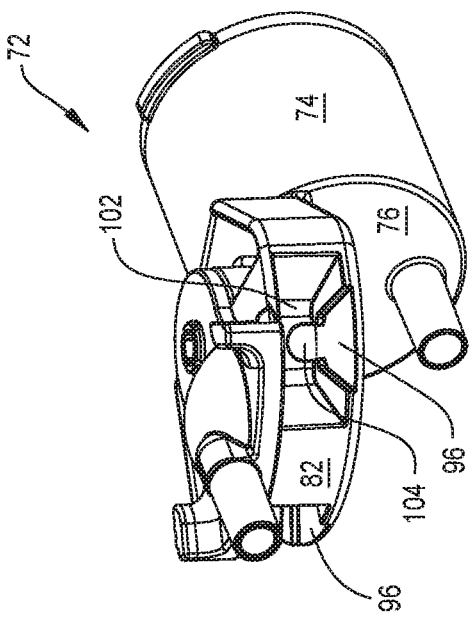

Cap 72, seen best in FIGS. 4, 7A and 7B, is formed to have a tube like base 74. Base 74 has an open proximal end. The cap 72 is formed so the open end of base 74 seats over the open distal end of the shell 64. Not identified and not part of the present invention are the fingers that extend forward from the shell 64 and the complementary features internal to the cap base 74 that facilitate the snap securement of the cap 72 over the shell 64. A face plate 76 that extends over the distal end of the base 74 formed the front face of the cap 72.

A head 78, also part of the body of manifold 60, is integrally formed with and extends distally forward from the cap face plate 76. The head 78 is formed to have planar top and bottom faces 80 and 84, respectively. In FIGS. 4 and 7B only the edge of the bottom face 84 is identified. The head 78 also has an arcuately shaped front face front face 82. Front face 82 is the most distally located surface of the head 78. Head 78 is further formed so that immediately proximal to the front face 82 a step 86 is formed in the top of face 80. Step 86 is arcuate in shape. The surface of step 86 is understood to be recessed relative to the surface of the adjacent portion of the top face 80.

The head 78 is formed to so that a bore 88 extends inwardly from the surface of step 86. Bore 88 is centered on an axis the extension of which intersects the longitudinal proximal-to-distal axis through the manifold 60. Bore 88 does not extend completely through the head to the bottom faced 84. Instead, bore 88 opens into a longitudinally extending bore 89 that extends proximally longitudinally through the head 78. Bore 89 opens up into the portion of the void internal the body of the manifold defined by the cap base 74.

Manifold head 78 is further formed that plural voids 92 extend inwardly from the front face 82. In the illustrated version of the invention there are two voids 92. Voids 92 are symmetrically located on opposed sides of the proximal-to-distal longitudinal axis of the manifold 60. Voids 92 are thus located on opposed sides of the open end of bore 88. The head 78 is formed so that the internal walls of the head that define the sides of each opening taper inwardly towards each other, walls not identified. Each of these internal walls is located on a separate radial line. The radial lines along which these walls are located project outwardly from a common point located on the longitudinal center plane of the manifold. Head 78 is further shaped so that the portion of the head that defines the base of each void 92 includes a center surface 96 (surfaces 96 identified only in FIG. 7A) that is recessed relative to two opposed planar perimeter surfaces 98 (one surface 98 identified in each of FIGS. 5 and 7B). The proximal end of each opening 92 is defined by a wall 102 internal to the head 78, one wall 102 identified in FIG. 7A. Walls 102 are understood to be located inwardly relative to the front face 82. Head 78 also has two additional internal bores, bores 104, one bore 104 identified in FIGS. 2 and 7A. Each bore 104 extends proximally inwardly from an associated one of the inner walls 102. Each bore 102 extends to and terminates at the bore 89.

The head 78 is further formed so there are two openings 106 in step 86 as seen in FIG. 7B. Each opening 106 opens into a separate one of the voids 92. The openings 106 are located on the opposed sides of the opening into bore 88. Head 78 also has three indentations 108 that extend proximally inward from the distal arcuate edge of step 86, (one indentation identified in FIG. 7B). A first one of the indentations 108 is centered on a line that radiates from a line that extends from the axial center of bore 88. The remaining two of the indentations 108 are each centered on separate lines that radiate from the centers of the individual openings 106.

Manifold head 78 also has a closed end bore 112 that extends inwardly from the head top face 80. Bore 112 is disposed over and does not intersect bore 89. Bore 112, in planes perpendicular to the top to bottom longitudinal axis through the bore 112 has a shape of a truncated circle. The axis around which bore 112 is centered interests the center point from which the radial lines that define the sides of voids 92 emanate. Plural flexible fingers 114, two identified in FIG. 6, extend upwardly from the surface internal to head that defines the base of the bore. The illustrated versions of the invention there are four fingers 114. Fingers 114 are arcuately spaced apart from each other and are located on a circle that is centered on the longitudinal axis through the bore. The manifold head 78 is shaped so the fingers 114 project above the top face 82. Each finger 114 has an outwardly directed tip 116, one identified in FIGS. 2 and 7B. Each finger tip 116 extends radially outwardly from and arcuately around the outer surface of the finger 114 with which the tip is integral.

The head 78 is also formed with a groove 118 that extends inwardly from the top face 82. Groove 118 is arcuate in shape and centered on the axis around which bore 112 is centered. Head 78 is shaped so groove 118 is spaced radially outwardly and away from bore 112. The groove 118 extends further into the head 78 than bore 112. More particularly, the head 78 is formed so that groove 118 intersects bore 89 and both bores 104.

Head 76 is formed from plastic. At least the portion of the top face 82 of the head that forms the structural members that extend over voids 92 is transparent.

A web 120 extends outwardly from the cap face plate 76. Web 120 extends to the bottom face 84 of the head 78. Web 120 provides structural support for the head 78.

Figure 8:
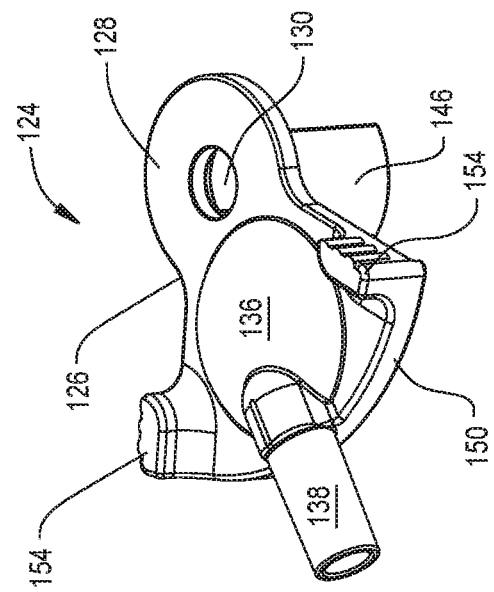
FIG. 8 is a perspective view of the bottom of the valve.
Figure 9:
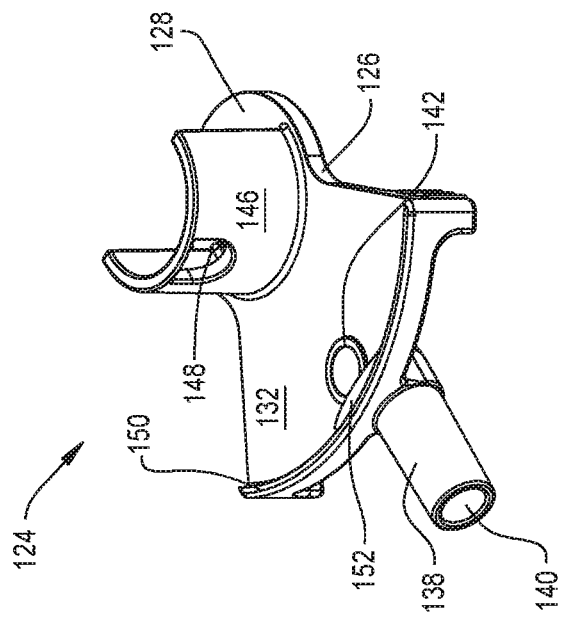
FIG. 9 is a perspective view of the top of the valve.
Figure 10:
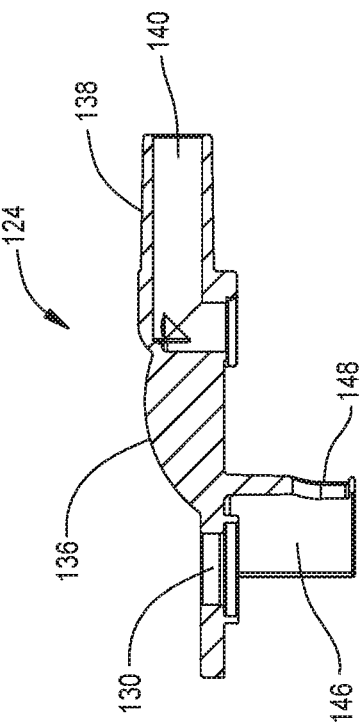
FIG. 10 is a is a cross sectional view of the valve.

A valve 124, also part of manifold 60, now described by reference to FIGS. 8 to 10 is moveably mounted to the head 78. Valve 124 includes a plate 126 that is disposed above the head top face 80. Plate 126 has a proximal section 128 that is generally circular in shape. The plate 126 has a distal section 132 that extends forward from an arcuate portion of the proximal section. The plate 124 is shaped so that, as the opposed sides of the plate distal section 132 extend forward from the proximal section 128, the sides taper outwardly. The front edge of the plate distal section 132 is arcuate in shape, edge not identified. Valve 124 is further formed so that an opening 130 extends top to bottom through the plate proximal section 128. Opening 130 is centered on the center of the plate proximal section 128. Opening 130 has a diameter slightly greater than the diameter of the circle defined by fingers 114 and less than the diameter of the circle defined by the finger tips 116.

As part of the assembly of manifold 60, valve 124 is fitted over the head 78, so fingers 114 and tips 116 extend through opening 130. The finger tips 116 extend outwardly beyond the portion of the plate 124 that defines the perimeter of opening 130. Fingers 114 thus rotatably hold the valve 124 to the rest of the manifold 60.

A dome 136 protrudes upwardly from the plate proximal section 132. More particularly, at least the dome 136 of valve 124 is formed from a transparent material, typically plastic. Dome 136 is shaped to magnify the view of objects disposed below the dome. The dome 136 is positioned so that, by selectively setting the rotational position of the valve, the dome can be located over the sections of the head 78 that defines either one of the voids 92.

Fitting 138 protrudes distally forward from the distally directed face of the dome 138. The fitting 138 is dimensioned to receive the proximal end of the suction line 50 through which a fluid stream is introduced into the manifold 60. A bore 140 extends proximally from the distal end of the fitting. Bore 140 extends a short distance into dome 138. The bore 140 is L-shaped. The short section of bore 140 extends perpendicularly downwardly from the longer distal-to-proximal long section of the bore. The short section of bore 140 extends through the dome and has an opening in the undersurface of plate distal section 132. This opening from bore 140 is positioned so that, depending on the rotational position of the valve 124 the opening can be placed in registration with opening into head bore 88 or either one of the openings 106. A ring 142 extends downwardly from the underside face of the plate distal section 132. Ring 142 surrounds the opening that leads out of bore 140. The ring 142 is dimensioned to fit in the space between step 86 integral with head 76 and the undersurface of the plate. Ring 142 prevents fluid loss or suction leakage between the head 78 and the fitting 138.

Valve 124 is further formed to have a stop 146 that extends downwardly from the undersurface of the plate proximal section 128. Stop 146 is in the form of a curved plate. When the valve 124 is mounted to rest of the manifold 60, stop 146 seats in groove 118 internal to the head 78. Stop 146 is formed to define a through hole 148. Hole 148 is centered around a top to bottom plane in which the longitudinal distal to proximal longitudinal axis of the fitting extends.

The valve 124 is also formed so a rim 150 projects around the outer distally directed curved end of the plate distal section 132. Rim 150 extends below the undersurface of the plate distal section 132. The rim 150 is located in front of the front face 82 of the head. A curved tab 152 extends proximally rearward from the proximally directed surface of the rim. Tab 152 is thus located below the undersurface of the plate distal section. The tab 152 is centered on the top-to-bottom plane in which the distal-to-proximal longitudinal axis through the fitting 138 extends. Tab 152 is dimensioned to seat in each of the indentations 108 formed in the manifold head 78. Finger grips 154 extend upwardly from the opposed ends of the rim 150.

The illustrated manifold 60 has a second fitting, fitting 156, identified in FIG. 6. Fitting 156 extends distally outwardly from the cap face plate 76. Fitting 156 opens into the void space internal to the manifold 60. Two backflow prevention valves 157, seen in FIG. 5, are mounted to the inner surface of the face plate 76. The individual backflow prevention valves 157 allow flow from the bore 89 and fitting 156 into the void space while blocking flow from the void space out through the bore 89 and the fitting 156. In the illustrated version of the invention, both backflow prevention valves 157 extend from a common hub (not identified). The hub is mounted to the inner surface of face plate 76 by a means not illustrated and not part of the present invention.

A filter 158 is disposed in the void space internal to the manifold 60. Filter 158 traps solid and semisolid material of a size larger than what should be held the canister 28 or 30 with which the manifold 60 is associated.

A catch tray 160, now described by reference to FIGS. 11-13, is removably seated in each one of the voids 92 formed in the manifold head 78. The catch trays 160 are formed from a single piece of elastomeric material such as plastic, rubber or silicone rubber. Each catch tray 160 includes a base plate 162. The base plate 162 has a proximal section 164 and a distal section 166. When the manifold 60 is aligned with the horizontal plane, the plate proximal section 164 is likewise in the horizontal plane. The plate distal section 166, extending distally from the distal end of the proximal section 164 angles upwardly from the proximal section 164. An end plate 168 extends perpendicularly upward from the proximal end of the plate proximal section 164. Opposed side plates 170 extend perpendicularly upward from the opposed sides of the tray base plate 162. Each side plate 170 extends to the adjacent end of the tray end plate 168. A front panel 172 extends perpendicularly upward from the distal end of the plate distal section 166. The front panel 172 extends around the whole of the distal perimeter of the plate distal section 166. The front panel 172 extends to and projects outwardly beyond the distal ends of each of the side plates 170.

As mentioned above, catch trays 160 are dimensioned to seat in the voids 92 internal to the manifold 60. Accordingly, each catch tray 60 has a shape that can be considered that of a truncated pie slice. The sides of the base plate 162, extending distally to proximally, taper towards each other. The opposed proximal and distal ends of the base plate 162 are curved. By extension both the end plate 168 and front panel 172 are curved in shape. Collectively, the features of the catch tray 160 are shaped so that, when the tray is seated in the manifold void 92, the outer perimeter of the proximally directed face of the front panel 172 seats against the perimeter portion of manifold face 82 that defines the opening into the void 92.

Each catch tray 160 is further formed so that the side panels 170 and front panel 172 extend below the distal section 166 of the base plate 162. Two webs 174, extend radially inward from the proximally directed face of the front panel to the undersurface of the distal section 166 of the base plate 162. The tray 160 is formed so that when the tray is seated in the associate void 92, the webs 174 rest on the perimeter surfaces 98 on either side of the recessed center surface 96 that defines the base of the void. A tab 176 extends outwardly from the outer face of the tray front panel 172. In the illustrated version of the invention, tab 176 has three panels. The tab 176 is dimensioned to facilitate the finger griping of the catch tray 160.

Each catch tray 160 is formed so that plural pores 169, one pore identified, extend through the end plate 168. Pores 169 are formed in the section of the plate 168, that when the tray is fitted to the manifold that is in registration with the open end of the bore 104 formed in the adjacent wall 102 internal to the manifold head. Pores 169 are dimensioned to allow fluid flow but are smaller is size than the samples the catch tray 160 is employed to trap. The tray base plate 162 is also formed to have the pores 169. Base plate 162 is formed so the pores 169 are located in the section of the plate between webs 174.

Manifold 60 of this invention is prepared for use by inserting a catch tray 160 in each of the voids 92. The manifold 60 is inserted in the receiver 40 of the waste collection unit 20 with which the manifold is used. As a result of this process the fitting 41 internal to the receiver 40 seats in opening 68 in the proximal end of plate 66. The fitting 41 extends past the drip stop 70. The drip stop 70 forms a barrier between the fitting 41 and the portion of plate 66 that forms the outer perimeter of opening 68. Fitting 41 thus provides a fluid communications path from the void space internal to the manifold 60 to the canister 54 or 56 with which the fitting 41 is associated.

Once manifold 60 is fitted to the receiver, suction line 50 is attached to the manifold and suction pump 58 turned on, waste collection unit 20 is ready for use.

Typically there is not an immediate need to trap a sample entrained in the fluid flow at the start of a procedure in which system 20 is employed. Accordingly, at the start of the procedure, the valve 124 is typically set in the bypass position. Valve 124 is in placed in the bypass position, by setting plate 126 so the opening in the distal end of bore 140 is in registration with the opening into bore 88. As a result of this positioning of valve 124, stop 146 assumes an orientation in groove 118 in which the through hole 148 internal to the stop is in registration with bore 88. On both sides of hole 148, sections of stop 146 interrupt the bores 104 that lead to bore 89. Stop 146 thus blocks the suction draw from openings 92 that would otherwise occur through bores 104.

Consequently when the valve 124 is in the bypass position, the fluid flow from the suction line 50 is through the fitting 138, through the bore 88 and 89 and into the void space internal to the manifold. If filter 158 is disposed in the manifold 60, solids and semisolids larger than the size of the pores internal to the filter are trapped by filter 158. The fluid flow out of the manifold through the receiver fitting 41 seated in the manifold outlet opening 68.

During the course of the procedure, there may be one or more instances in which it is so determined it is worthwhile to retain tissue that will flow through the fluid stream for further study. When it is determined that such a condition exists, the valve is rotated from the bypass position to the sample collection position. The valve 124 is placed in the sample collection position by rotating the plate 126 so the opening in the distal end of the bore 140 is placed in registration with one of the openings 106 in the manifold head 78. As a result of the valve being so positioned, the stop 146 is rotated so hole 148 moves into registration with the bore 104 associated with the opening 106. The solid arcuate section of the stop 146 to the side of the bore interrupts both bore 89 and the remaining bore 104. Stop 146 thus continues to block the suction draw through the non-selected bore 104 as well as the bypass bore 89.

When valve 124 is in the specimen collection position, the fluid stream thus flows from the fitting 138 into the open top of the catch tray 160 in the void space 96 into which the opening 106 opens. The fluid stream flows through the void space, through the pores 169 in the catch tray and into the bore 104. Owing to the void 92 having a recessed base, a fraction of this fluid flow is through the pores 169 in the tray base plate 162. The remaining fraction of this flow is through the pores 169 in the tray end plate 168. The sample, which is larger is size than pores 169, is trapped in the catch tray 160. From the bore 104 the fluid flows into bore 89. From bore 89 the fluid flows in the same path as when the valve is in the bypass position.

During the process, the practitioner may look through dome 136 to determine when the sample becomes trapped. Owing to the geometry of the dome 136, the view the practitioner sees in the trap is magnified. This facilitates the prompt visual detection regarding whether or not the sample targeted for retrieval has been trapped.

After the sample is trapped, the procedure may be in a state in which there is not an immediate need to capture an additional sample. If the procedure is in this state, the valve is returned to the bypass position. The fluid stream then simply returns to the state of flowing from the fitting and bores 88 and 89 into the manifold void space.

Alternatively, almost immediately after one sample is trapped, it may be necessary to trap a second sample. If this condition exists, valve 124 is set so the fitting is placed in registration with the second opening 106. This causes the fluid stream to essentially immediately flow through the second catch tray 160. This makes it possible to trap a second sample, even if, owing to the timing of events it is not possible to replace the first catch tray 160 removed from the manifold in order to collect and store the first sample.

Once the valve 124 is shifted away from the specimen collection position with which a particular catch tray 160 is associated, the catch tray can be removed from the void 92 in which the tray is seated. A new catch tray can be seated in the void 92. This means valve 124 can be returned to the specimen collection position in which a fluid stream that contains a specimen to be collected is flows through the void 92 in which an earlier specimen was collected. This newly selected specimen will be trapped in its own tray 160. The trays are often provided with means for the personnel to include data that indicates from where in the patient the specimen was collected.

The cassette 60 of this invention thus allows the practitioner to capture plural samples, each in its own catch tray 160, with essentially no interruption of the drawing of the fluid stream in which the samples are entrained. Since each sample is contained in its own catch tray 160, there is minimal effort associated with correlating the sample with the location on or in the patient from which the sample was extracted. This facilitates the proper diagnosis of the state of the patient.

It is a further feature of this invention that the valve 124 is bifunctional. The valve 124 does more than simply direct the fluid flow through either the bypass conduit, bore 88 in the described version of the invention, or into a catch tray 160. Valve 124 and more particularly, stop 146, when the valve is in the bypass states, blocks suction draw from the catch trays 160. When the valve is set to facilitate sample capture, the stop 146 blocks of suction draw from the bypass conduit and the catch tray not being used for capture. One benefit of this feature of this invention is that it substantially eliminates suction leakage through the flow paths through which the fluid stream is not being routed. A second benefit of this feature is that it reduces the noise that might be otherwise generated if suction is drawn on these non-selected flow paths.

As the valve 124 rotates the tab 152 integral with the valve seats in and rotates out of the indentations 108 in the body of the manifold 60. The varying resistance of the valve 124 as the tab so rotates provides tactile feedback regarding the setting of the valve.

It should be appreciated that the above is directed to specific versions of the invention and that other versions of the invention may have features different from what has been described. For example, this invention is not limited to versions of the invention in which the cassette is formed with two voids for receiving separate catch trays. In alternative versions of the invention the cassette may include void spaces for receiving three or more catch trays.

Figure 14:
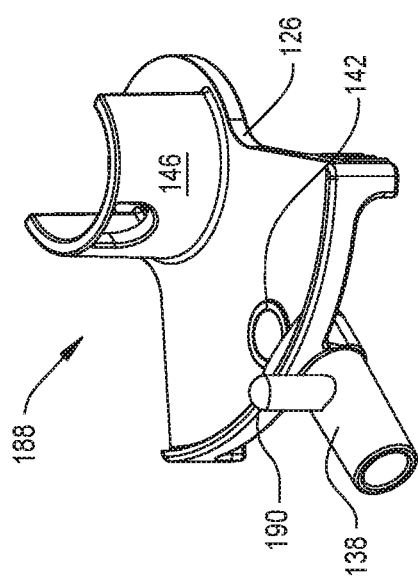
FIG. 14 is a perspective view of an alternative valve of this invention.

FIG. 14 illustrates an alternative valve 188 that can be employed as part of the cassette of this invention. Valve 188 includes essentially all the features of valve 124. Accordingly, the majority of these features are not redescribed. Valve 188 also includes a tab 190, seen as a cylindrical member, that extends downwardly from fitting 138. Tab 190 is positioned to be located forward of front face 82 of head 78 of cassette 60.

Figure 15:
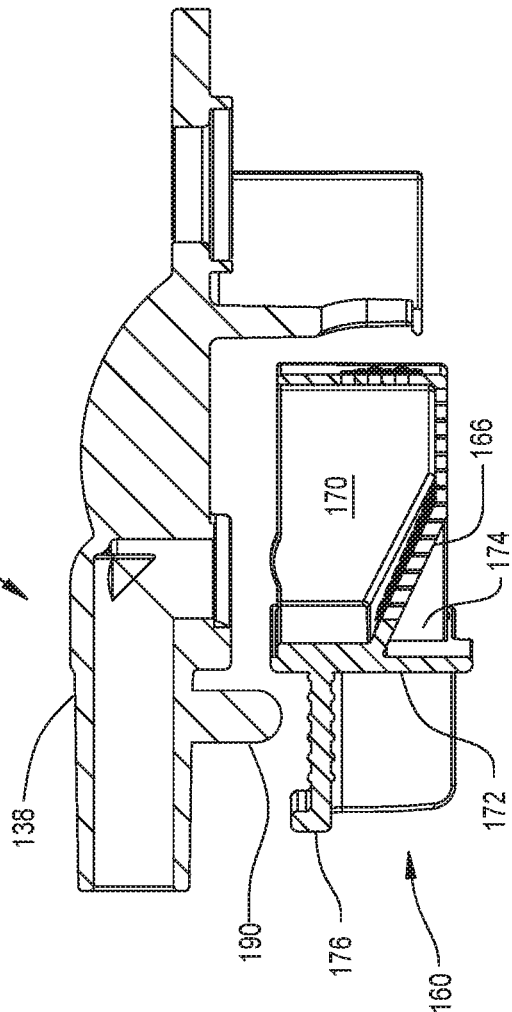
FIG. 15 is a cross sectional view of the position of the valve of FIG. 14 to a catch tray when the valve is in specimen collection position so as to direct the fluid flow into the catch tray.

FIG. 15 depicts where tab 190 is located when the valve 188 is in the specimen collection position. In FIG. 15 only the catch tray 160 and valve 188 are shown. The portions of the cassette head 78 in which the catch tray is seated and to which the valve is attached are not illustrated. As seen in this Figure, when valve 188 is in this position, tab 190 is located immediately in front of the front panel 172 of the catch tray 160 through which the valve 188 directs the fluid stream. Tab 190 thus functions as a lock out for the cassette with which the valve 188 is integral. Specifically, when the valve 188 is in the specimen collection position, the tab 190 prevents the withdrawal of the catch tray 160 through which the valve is directing the fluid flow. This substantially eliminates the likelihood that a catch tray 160 can be removed during times when, owing to the position of the valve and stop, a suction is being drawn on the space in which the catch tray is seated. Preventing removal of the catch tray when the cassette is in this state results in a like prevention that the suction drawn on this space will result in the unintended draw of the specimen out of the tray.

When valve 188 is moved to the bypass position, the stop 146 moves to a position in which the stop blocks the suction draw on the tray-receiving void 92. The movement of the valve 188 also causes tab 190 to move to a position in which the tab is spaced from the catch tray 160. Catch tray 160 therefore can only be removed when the cassette is a state in which a suction is not being drawing on the void 92. This means that when the tray is withdrawn, there is essentially no likelihood that the suction that is continually drawn through the outlet opening will result in the draw of the trapped specimen out of the tray.

It should be understood that stop 146 performs two functions. The stop prevents a draw of suction on the non-selected opening 88, 106. This prevents the loss of suction through the flow path, opening 88 and bore 89 or, if the valve is in the collection position, the selected opening 106 and associated void 92. The second function stop 146 is that when the valve 124 or 188 is spaced from a void space 92, the valve prevents the draw of suction which could result in the loss of the specimen just trapped in the catch tray 160.

It should likewise be understood that while the stop 146 and tab 160 move with the valve, there is no requirement that in all versions of the invention one or both of these components be formed to be integral with the valve. In some versions of the invention one or both of the stop 146 and tab 160 may be separate from the valve. A link or a gear may connect the separated stop or tab so that when the valve moves, the disconnected stop or tab engage in the appropriate motion. Specifically, when the valve is in specimen collection position, the tab or other lock feature is positioned to prevent the catch tray 160 from being removed from the void space. Also when the valve is in the specimen collection position, the stop 146 is set to allow suction to be drawn on the void 92 in which the tray is seated. When the valve is moved away from the void 92 holding that particular tray 160, stop 142 moves to a position in which the stop blocks the draw of suction on the void space in which the tray is seated. Tab 190 or other lock feature moves away from the tray so as to allow removal of the tray. In some versions of the invention the components are designed so that only after the stop 190 is set to block suction through a void 92 does the tab or other lock feature move into a position in which the lock feature no longer prevents removal of the tray 160.

Likewise this invention is not limited to versions of the invention wherein the valve that sets the state of the cassette between the bypass state and the sample capture state rotates. In alternative versions of the invention, for example the valve may be attached to the cassette to engage in translation movement. If the catch tray-holding void spaces are arranged linearly in the body of the cassette, the valve may be mounted to the cassette to move linearly. If the catch tray holding void spaces are arranged arcuately around the body of the cassette, the valve may be mounted to the cassette to engage in an arcuate translation motion.

Likewise, it should be understood that there is no requirement that in all versions of the invention, the fitting through which fluid flows to the valve be part of the valve. Thus, it is within the scope of this invention that the fitting be static relative to the rest of the cassette. In these versions of the invention, the valve regulates the flow from the fitting so the fluid stream flows through the bypass conduit or one of the catch tray-holding void spaces.

Also, it may be desirable to, in some versions of the invention, provide the cassette body with plural bypass conduits. This would be useful in versions of the invention where the cassette holds three or more catch trays. In these versions of the invention it may be necessary to provide a bypass conduit between each pair or catch tray-holding void spaces. In these versions of the invention the valve may have two or more position in which the valve can be set to facilitate bypass flow. A benefit of these versions of the invention is that it both lessens the time required to reset the valve from the specimen trap position to the bypass position. A further benefit of this version of the invention is that reduces the likelihood that, when resetting the valve from the specimen trap position to the bypass position, the valve position will result in fluid being momentarily routed through one of the catch trays. Should this event occur, there is possibility that the material not needed as a specimen will be inadvertently captured in the catch tray.

Some versions of the invention may have space for removably receiving only a single catch tray.

It should be appreciated that other versions of the invention may have features different from what has been described. For example, there is no requirement that all cassettes of this invention be provided with the described drip stop 70, bypass fitting 156 or filter 158. There is no requirement that in all versions of the invention, the valve and stop be a single piece unit. In some versions of the invention, a link connected between the valve and the stop displaces the stop into the correct position when the valve is set.

Likewise the shapes of the features may vary from what has been described. If the cassette of this invention is not designed to seat in the circular bore of a receiver, there is no need for the cassette to have a circular body. Likewise, there is no requirement that the void spaces for receiving the catch trays be pie-shaped. Thus these void spaces and the catch trays may have shapes different from what has been described. Likewise, some cassettes of this invention may not have a void space for receiving the fluid from a bore similar to bore 89. In these versions of the invention a proximal end of a bore analogues to bore 89 may serve as the open end of the cassette that is connected to the suction source. It may not be necessary in all versions of the invention to construct the catch tray so that fluid flow is through plural plates of the tray. In some versions of the invention this flow may be through only one of the plates, typically either the base plate or the end plate.

It similarly is understood the catch trays may not always be tray like in shape. In some versions of the invention, these trays may be elongated structures, that is, structural that have a top-to-bottom height greater than the side-to-side width and/or front-to-back depth.

In some versions of the invention one or both of the cassette and catch trays are provided with latch features. These latch features inhibit the unintended removal of the catch trays from the cassette.

The components from which the cassette of this invention are formed may likewise be different from what is described. For example, there is no requirement that, in all versions of the invention, valve 124 be formed from a single piece of material. In some versions of the invention, while most of the valve 124 is formed from a hard plastic, one or both of the ring 142 and stop 146 may be formed from a compressible material, such as rubber. In some versions of the invention, these compressible components are molded into the rigid plastic that forms the rest of the valve 124. Forming the ring 142 and/or stop out of a compressible material facilitates the fluid blocking features of these components.

In versions of the invention in which ring 142 is formed out of the compressible material, it may further be useful to design the components that hold the valve 142 to the head 78 so that these components urge the valve against the head. This may be accomplished by the appropriate sizing of the length of the fingers 114 that rotatably hold the valve 142 to the head. A benefit of this construction of the invention is that when the valve 124 is seated on the head 78, ring 142 is compressed between the face 80 of the head 78 and the valve plate 126. This facilities the formation of the seal by the ring 142 between the face 80 and the valve plate 126.

In versions of the invention in which stop 146 is formed from compressible material, it may be advantages to form the stop to have a proximal-to-distal thickness thereacross that is marginally greater (0.1 to 1.0 mm) than the width of the groove 118 in which the stop is seated. A benefit of this construction of the invention is that when the stop 146 is seated in groove 118, the stop is compressed. This increases the fluid blocking ability of the stop 146. In some embodiments of this version of the invention, only sections of the stop are formed from compressible material. For example, there may be a frame of flexible material around the portion of the stop 146 that defines the opening 148. This provides the desired seal while minimizing the frictional resistance the compressible material places on the manual displacement of the valve 124 or 188.

Other assemblies than the disclosed tab 190 may be provided to lock out the removal of a catch tray 160 when the valve 188 is seat to direct the fluid stream through the catch tray. For example, in some versions of the invention, the components may be arranged so that, when the catch tray is seated in the complementary void internal to the body of the cassette, the front panel is recessed inwardly relative to the face of the panel through which the tray is inserted and withdrawn. In these versions of the invention, the lock out component may be a member that extends through a slot in the cassette body in front of the catch tray.

In some versions of the invention the cassette and catch tray are provided with complementary features to ensure that, when the tray 160 is seated in the associated void 92, the tray is in the correct orientation in the void.

Further, it may be desirable to provide the tray with a surface on which it is possible to write information. This would make it possible to write data related to the specimen that is captured in the tray.

Accordingly, it is an object of the appended claims to cover all such modifications and variations that come within the true spirit and scope of the invention.

What is claimed is:

1. A cassette for collecting tissue sample from a fluid stream, said cassette comprising:
   a body comprising an exposed face and defining an outlet opening through which a suction is adapted to be drawn, a tray-receiving void extending inwardly from the exposed face and forming a flow path with the outlet opening, and a bypass conduit defined by the body and forming a bypass flow path bypassing the tray-receiving void;
   a catch tray removably mounted in the tray-receiving void and adapted to allow fluid flow therethrough towards the outlet opening while retaining material above a certain size;
   a valve comprising a fitting for receiving a suction line and being moveably mounted to the body to receive the fluid drawn into the fitting, the valve adapted to direct the fluid flow from the fitting into either the bypass conduit or the tray-receiving void, wherein the catch tray is adapted to be removed from and reinstalled in the tray-receiving void with the valve positioned to direct the fluid flow into the bypass conduit;
   a lock feature coupled to the valve and comprising a projection movably positioned forward of the exposed face such that, when the valve is positioned to direct the fluid flow into the tray-receiving void, interfere with the catch tray to inhibit removal of the catch tray from the tray-receiving void, and wherein the lock feature is further configured to, when the valve is positioned to direct fluid flow into the bypass conduit, be spaced from the tray-receiving void so as to allow removal of the catch tray from the tray-receiving void; and
   a stop member coupled to the valve and movable relative to the body such that, (i) when the valve is positioned to direct the fluid flow into the tray-receiving void, the stop member is adapted to block the fluid flow through the bypass flow path, and (ii) when the valve is positioned to direct fluid flow into the bypass conduit, the stop member is adapted to block the fluid flow through the flow path.

2. The cassette of claim 1, wherein the valve and the lock feature are a single piece component.

3. The cassette of claim 1, wherein the catch tray comprises a plurality of catch trays with the tray-receiving void being a plurality of tray-receiving voids each for receiving a respective one of the plurality of catch trays.

4. The cassette of claim 1, wherein the lock feature is positioned outwardly relative to the exposed face.

5. A cassette for collecting tissue sample from a fluid stream, said cassette comprising:
   a shell defining an outlet opening through which suction is to be drawn;
   a cap comprising a cap base coupled to the shell to define a void internal to the cassette, and a cap face plate at a distal end of the cap base to form a front face of the cap, wherein the cap further comprises:
      a cap head extending distally forward from the cap face plate, the cap head comprising an exposed face and defining a plurality of tray-receiving voids extending inwardly from the exposed face and opening into internal bores, and a bypass conduit forming a bypass flow path that bypasses the plurality of tray-receiving voids, wherein each of the internal bores and the bypass conduit merge into a main bore that opens to within the shell;
      a valve movably mounted to the cap head and comprising a fitting for receiving a suction line through which fluids are adapted to be drawn away from a patient, wherein the valve is adapted to direct the fluid flow from the fitting into either the bypass conduit or one of the plurality of tray-receiving voids; and
   a plurality of catch trays each separately and removably mounted in one of the plurality of tray-receiving voids, one of the plurality of catch trays is adapted to be removed from and reinstalled in one of the plurality of tray-receiving voids with the valve positioned to direct the fluid flow through another one of the plurality of catch trays.

6. The cassette of claim 5, wherein the cap head defines an opening into the bypass conduit located between two of the tray-receiving voids so that, as the valve is moved from a first one of the tray-receiving voids to a second one of the tray-receiving voids, the valve directs the fluid flow into the bypass conduit.

7. The cassette of claim 5, further comprising a filter element disposed within the cap base.

8. The cassette of claim 5, wherein the valve is rotatably mounted to the cap head.

9. The cassette of claim 5, wherein the plurality of tray-receiving voids is two tray-receiving voids with each of a first and a second tray-receiving void is configured to receive one of the plurality of catch trays.

10. The cassette of claim 9, further comprising a stop member coupled to the valve and movable relative to the cap head, wherein the stop member is configured to block the fluid flow through one of the flow path and the bypass flow path based on the position of the valve.

11. The cassette of claim 10, wherein the cap head defines a groove in communication with the bypass conduit and the flow path, wherein the groove sized to receive the stop member to be compressed within the groove.

12. The cassette of claim 10, wherein the valve and the stop member are a single piece component.

13. The cassette of claim 5, further comprising a filter element disposed within the body within the flow path and the bypass flow path.

14. The cassette of claim 5, wherein the tray-receiving voids are at least partially defined by a wall opposite the exposed face with the wall defining a bore.

15. The cassette of claim 5, wherein the exposed face is arcuate in shape.

16. The cassette of claim 5, wherein the fitting is a first fitting with said cassette further comprising a second fitting extending from the cap face plate and separate from the first fitting, wherein the second fitting is adapted to receive another suction line to establish a third flow path from the second fitting to the outlet opening that is separate from the flow path and the bypass flow path.

17. The cassette of claim 5, further comprising a lock feature coupled to the valve and configured to, when the valve is directing the fluid flow into one of the tray-receiving voids, inhibit removal of the respective one of the catch trays from the respective one of the tray-receiving voids.

18. A cassette for collecting tissue sample from a fluid stream, said cassette comprising:
   a body comprising a shell defining an outlet opening through which suction is to be drawn, and a cap coupled to the shell to define a void internal to the cassette, wherein the cap comprises an exposed face and defines:
      a plurality of tray-receiving voids extending inwardly from the exposed face;
      internal bores with each of the plurality of tray-receiving voids opening into a respective one of the internal bores;
      a bypass conduit forming a bypass flow path that bypasses the plurality of tray-receiving voids;
      a main bore, wherein each of the internal bores and the bypass conduit open into the main bore with the main bore opening into the void internal within which a filter element is disposed;
   a plurality of catch trays separately and removably mounted in the tray-receiving voids; and
   a valve comprising a fitting for receiving a suction line through which fluids are adapted to be drawn away from a patient, the valve being moveably mounted to the body and adapted to direct the fluid flow from the fitting into either the bypass conduit or one of the tray-receiving voids, wherein one of the plurality of catch trays is adapted to be removed from and reinstalled in one of the tray-receiving voids with the valve positioned to direct the fluid flow through another one of the plurality of catch trays removably mounted in another one of the tray-receiving voids.

* * * * *